US008480396B2

(12) United States Patent
Saliger et al.

(10) Patent No.: US 8,480,396 B2
(45) Date of Patent: *Jul. 9, 2013

(54) METHOD FOR AUTOMATICALLY FABRICATING A DENTAL SUPERSTRUCTURE FOR ATTACHMENT TO AN IMPLANT

(75) Inventors: Gunter Saliger, Bensheim (DE); Bernd Rothenberger, Gernsbach (DE); Reinhard Pieper, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/447,995

(22) Filed: Apr. 16, 2012

(65) Prior Publication Data

US 2012/0203366 A1   Aug. 9, 2012

Related U.S. Application Data

(60) Continuation of application No. 13/015,646, filed on Jan. 28, 2011, now Pat. No. 8,167,617, which is a division of application No. 10/541,010, filed as application No. PCT/DE03/04252 on Dec. 31, 2003, now Pat. No. 7,901,209.

(30) Foreign Application Priority Data

Jan. 2, 2003   (DE) .................................. 103 00 301

(51) Int. Cl.
*A61C 5/00*   (2006.01)
(52) U.S. Cl.
USPC ......................................................... 433/215
(58) Field of Classification Search
USPC .......... 433/223, 215, 172–176, 167; 700/163, 700/182
See application file for complete search history.

(56) References Cited

U.S. PATENT DOCUMENTS

| 4,837,732 A | 6/1989 | Brandestini et al. |
| 4,988,297 A | 1/1991 | Lazzara et al. |

(Continued)

FOREIGN PATENT DOCUMENTS

| AU | 762679 | 1/2001 |
| DE | 196 54 055 A1 | 6/1998 |

(Continued)

OTHER PUBLICATIONS

Mormann, "CAD/CIM in Aesthetic Dentistry," Quintessence Publishing Co., Inc, Jan. 15, 1996, pp. 427-440.

(Continued)

*Primary Examiner* — Sunil K Singh
(74) *Attorney, Agent, or Firm* — Fitzpatrick, Cella, Harper & Scinto

(57) ABSTRACT

A system for a dental superstructure to be attached to an implant using a digital model description of a shape of the superstructure, the superstructure including first and second elements. The system comprises a computing device arranged to (a) analyze a recorded real clinical situation or shaped clinical situation of an implant axis and insertion axis, (b) compute a shape of the dental superstructure based at least in part on the determined implant axis, (c) generate digital data representing the shape of the superstructure, and (d) separate the computed shape into first digital data representing a shape of the first element to be connected to the implant and second digital data representing a shape of the second element to be connected to the first element, the shape of the first element being optimized, at least in part, based on a tilt angle between the determined implant axis and insertion axis.

17 Claims, 6 Drawing Sheets

U.S. PATENT DOCUMENTS

| | | | |
|---|---|---|---|
| 5,092,022 A | 3/1992 | Duret | |
| 5,273,429 A | 12/1993 | Rekow et al. | |
| 5,359,511 A | 10/1994 | Schroeder et al. | |
| 5,716,215 A | 2/1998 | Blacklock | |
| 5,989,029 A | 11/1999 | Osorio et al. | |
| 6,126,445 A * | 10/2000 | Willoughby | 433/223 |
| 6,224,371 B1 | 5/2001 | De Luca | |
| 6,231,342 B1 | 5/2001 | Osorio et al. | |
| 6,398,554 B1 | 6/2002 | Perot et al. | |
| 6,788,986 B1 | 9/2004 | Traber et al. | |
| 6,968,247 B2 | 11/2005 | Rathke et al. | |
| 7,086,863 B2 | 8/2006 | Van der Zel | |
| 2002/0090592 A1 | 7/2002 | Riley et al. | |
| 2006/0106484 A1 | 5/2006 | Saliger et al. | |

FOREIGN PATENT DOCUMENTS

| | | |
|---|---|---|
| EP | 0 250 993 B1 | 11/1991 |
| EP | 0 850 601 A2 | 7/1998 |
| EP | 0 904 743 A2 | 3/1999 |
| EP | 1 023 876 A2 | 8/2000 |
| EP | 1 062 916 A2 | 12/2000 |
| EP | 1 252 867 A1 | 10/2002 |
| JP | 10-277059 | 10/1998 |
| WO | 03/024352 A1 | 3/2003 |
| WO | 2004/060197 A1 | 7/2004 |

OTHER PUBLICATIONS

Kucey, B., et al., "The Procera Abutment—The Fifth Generation Abutment for Dental Implants," Journal of the Canadian Dental Association, vol. 65, No. 8, pp. 445-449 (Sep. 2000).

PCT International Preliminary Examination Report dated Dec. 31, 2003, regarding International Application No. PCT/DE2003/004252 (and English translation thereof).

European Patent Office, "Entscheidung über den Widerruf des Europäischen Patents," pp. 1-7, May 21, 2010 (and English translation thereof).

At least partial English machine translation of "Bego of Bremen Goldschlagerei . . .", 17 sheets, Oct. 2, 2009.

At least partial English machine translation of "Straumann holding AG" ("Objection against the German patent 103 00 301 B4"), 32 sheets, Oct. 2, 2009.

European Patent Office, "Übersendung der Abschrift der Niederschrift nach Regel 124 (4) EPÜ," 15 sheets, May 21, 2010.

Schulz, H., "Modellation and Anatomie der Zahnkrone," Verlag Neuer Merkur GmbH, Munchen, DE, 1997, pp. 7-9 (and machine-generated English translation thereof).

Mormann, "CAD/CIM in Aesthetic Dentistry," Quintessence Publishing Co., Inc, Jan. 15, 1996, pp. 361-368.

* cited by examiner

METHOD FOR AUTOMATICALLY FABRICATING A DENTAL SUPERSTRUCTURE FOR ATTACHMENT TO AN IMPLANT

CROSS REFERENCE TO RELATION APPLICATIONS

This application is a continuation of U.S. patent application Ser. No. 13/015,646, filed Jan. 28, 2011, which is a division of U.S. patent application Ser. No. 10/541,010, filed Jun. 28, 2005, now U.S. Pat. No. 7,901,209, which is a national phase filing under 35 U.S.C. 371 based on International Patent Application No. PCT/DE2003/004252, filed Dec. 31, 2003, which claims priority to German Application No. 103 00 301.0, filed Jan. 2, 2003. The contents of each of those applications is hereby incorporated by reference, as if set forth fully herein.

BACKGROUND OF THE INVENTION

1. Field of the Invention

The invention relates to a method of automatically fabricating a dental superstructure, in particular an abutment possessing geometry for attachment to a dental implant. The superstructure may consist of one or more elements. In multi-element superstructures for attachment to dental implants, one element of the superstructure, namely the abutment, serves the biomechanical as well as the esthetic purpose of compensating for the angular difference between the axis of the implant and the occlusal direction in order to ensure that the masticatory forces are properly transferred to the implant in esthetically feasible solutions.

The purpose of an abutment is, among other things, to provide on its side oriented toward the jaw perfectly fitting means of attachment to the implant and to provide on its side oriented toward the oral cavity a structure that can be fitted with conventional prosthetics. In order to fulfill the second requirement in particular, the side of the abutment oriented toward the oral cavity has a post-like appearance. The post follows the axis of the tooth to be replaced. This axis is perpendicular to the occlusal surface of the teeth, especially in the case of molars.

2. Description of the Prior Art

The shapes of individual abutments have hitherto been determined by dental technicians or by the attending dentist.

Only standard abutments are used in prior art technology. Standard abutments having fixed tilt angles are available on the market for compensating the angle between the implant axis and the occlusion.

The procedure described in EP 1 062 916 A2 is based on inserting a so-called manipulation implant into a conventional cast and in this manner creating a situation in the model that simulates the situation in the patient's mouth after the implant has been introduced. This clinical set-up is then scanned for the purpose of producing an abutment and, if needed, an associated second element of the superstructure. An auxiliary device is used for scanning. With this procedure, the tasks that the dental technician must perform in prior art technology are simulated with the aid of a computer, ie, on the basis of a digitized 3D model, the necessary intermediate steps of modeling the abutment, the frame, and the veneer being performed in the computer in order to enable production of the final superstructure by means of a computer-controlled grinding machine. This is known as a CAD/CAM process.

Methods are disclosed in U.S. Pat. No. 5,989,029 and U.S. Pat. No. 6,231,342 for computation of a customized abutment from several scans carried out in different directions by modification of a standard abutment. With such methods, however, it is still necessary to make a dental impression.

It is an object of the invention to make it possible to design the shape of a customized abutment automatically within specific limits.

Determination of the compensating angle between the implant and the axis of the tooth, in addition to the outer design of the crown in relation to the occlusion, is critical for the proper functioning and esthetics of the superstructure.

SUMMARY

A method of automatically fabricating a multi-element superstructure, in particular an abutment with a crown, to be attached to an implant with the help of a digital model description of the shape, consists of recording the clinical situation or a shaped clinical situation of the implant as digital data, analyzing this situation and determining the implant axis, computing the optimum shape of the superstructure, and fabricating the individual elements from one or more blanks of a given material with the aid of said digital data using machining equipment.

The clinical situation corresponds to the actual situation in the patient's mouth. The shaped clinical situation is different in that methods such as modeling the gums by wax build-up or determining the gingival profile with the help of a data set are employed.

By this means it is also possible to include the attachment surface between the first element and the second element when computing the outer contour of the two-element superstructure. A suitable first element is, in particular, an abutment, a suitable second element being a crown. In the method of the invention, the separation of the superstructure into abutment and crown and shaping of the abutment are accomplished automatically. In doing so, the optimal customized shape of the abutment is created automatically according to the geometric, clinical, material and fabricating technology aspects.

In general the various parts of the superstructure are produced from different blanks. In some circumstances it is possible to use a single blank for the manufacture of both the first and the second element of the superstructure.

According to one development, a mating surface between the digitally displayed first element of the superstructure and the digitally displayed second element of the superstructure is determined and taken into account during fabrication.

The remaining form of the superstructure is advantageously described by at least two of the following parameters: the shoulder width, the angle of the superstructure in relation to the longitudinal axis of the implant, the angle of rotation of the superstructure about the longitudinal axis within the blank, and the height of the post.

The profile of the edge of the superstructure is such that it lies inside the blank used. The interfacial line between an upper element of the superstructure, for example a crown, and a lower element of the superstructure, for example an abutment, is designated as an edge. For esthetic reasons, this edge should lie either flush with or below the gingival margin. The edge of the superstructure is determined either from a given clinical situation or from a shaped clinical situation.

By "dental superstructure" we mean any component that can be directly attached to an implant. In particular, these are abutments, but they can alternatively be telescopes, etc.

The description of the shape or edge is provided as digital data in the form of a line, surface, or scattergram, or alternatively parametrically. The shape of the entire superstructure can be digitally depicted as consisting of outlines, as a plane, as a scattergram, and/or as a parametric description. Depiction with an outline and a set of parameters has been chosen here by way of example.

According to one development, the shape of an abutment is optimized by means of one or more or all of the following parameters, namely the minimum shoulder width; the maximum post height, as determined by the tilt angle relative to the occlusal direction, the block geometry, and the height of the occlusal surface; the maximum post height, which is such that it is below the occlusal surface by a certain maximum distance; the minimum post height, which is delimited by the location of the head of an occlusal screw; and the angle of rotation of the abutment about the longitudinal axis within the blank, which is given by the relative position of the implant in the clinical situation.

This optimization is achieved automatically with the aid of the digital data provided by the appropriate software, and the result is digital data that describe the abutment to be produced. These data may be made visible for monitoring purposes by appropriate means, for example, by displaying a three-dimensional model on a screen.

The shape of the blank and the shape of the dental superstructure are advantageously described in the coordinate system of the geometry for attachment to the implant. The implant attachment geometry is a fixed geometry found in the implant as well as the blank and in the superstructure to be fabricated, and is produced with great precision. This circumstance makes it is possible, through skilled selection of a coordinate system, to dispense with conversion between different coordinate systems. In general, however, any known coordinate system is sufficient, for example, the one used during scanning.

In problematic, ie, ambiguous cases, the implant axis can be advantageously determined interactively by the user.

Additional embodiments of the method are disclosed in the subclaims.

BRIEF DESCRIPTION OF THE DRAWINGS

The method of the invention is illustrated below with reference to the drawings, in which.

DETAILED DESCRIPTION

Figure 1:
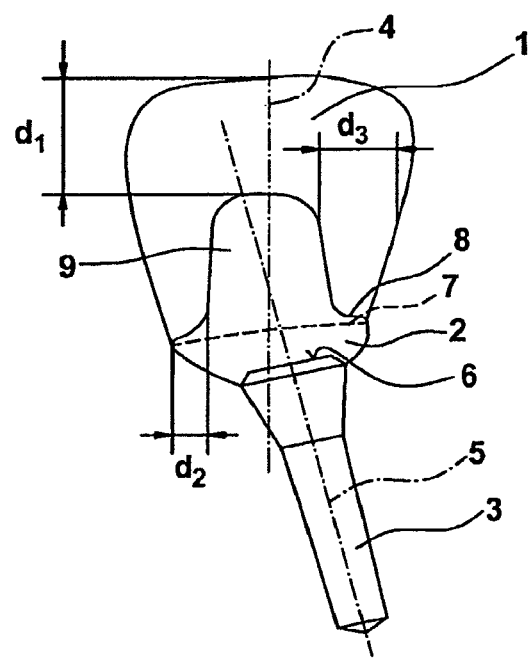
FIG. 1 is a diagram of a two-element superstructure for a dental implant.

FIG. 1 is a diagram of a two-element superstructure, composed of a crown 1 and an abutment 2, on an implant 3. The insertion direction of crown 1 is indicated by an axis 4.

The position of implant 3 in the jawbone is illustrated by an additional axis 5. Axes 4 and 5 only rarely coincide, because the insertion position of the implant in the clinical situation is dependent on the patient and must be defined on the one hand in relation to the bone material available and on the other hand in relation to the existing teeth. These parameters are critical for correct positioning and orientation of the implant to ensure future mechanical stability during the process of chewing. The position of the implant with its axis 5 may therefore differ from the position of the original root of the tooth.

Abutment 2 is joined to the end of implant 3 at the level of the jawbone by a form-fitting attachment geometry 6. The ideal abutment shape expands from the geometry for attachment toward the implant in such a way that it forms with its abutment edge 7 a tooth cross section approx. 1 mm below the gum (gingiva).

The abutment shape provides a shoulder 8 above and around abutment edge 7, on which crown 1 rests. This shoulder 8 is wide enough to ensure that the wall thickness of the crown is not less than the minimum value specified for the material. Shoulder 8 merges into a post 9 of smaller diameter.

This post 9 points in the insertion direction indicated by axis 4. Ideally, abutment 2, by its shape, compensates for the angle known as the tilt angle between implant axis 5 and the insertion direction in such a way that crown 1 can be mounted in the occlusal direction along axis 4 (see FIG. 3).

Instead of the occlusal direction, any other axis can be employed, such as a common insertion axis for the upper element of the two-element superstructure in a superstructure for multi-membered dental restorations.

Figure 2A:
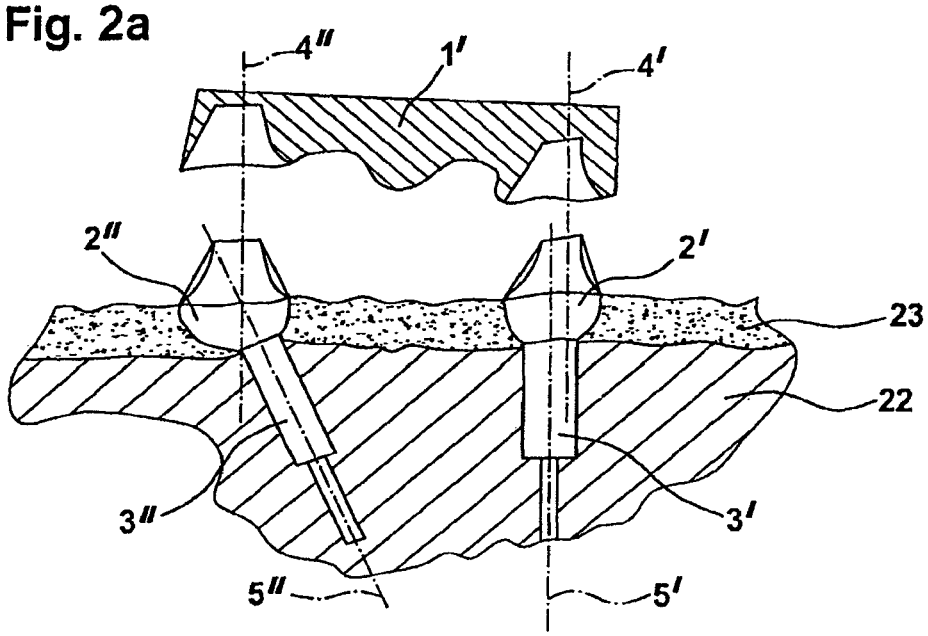
FIGS. 2a and 2b show a clinical situation with two implants inserted in the jaw.
Figure 2B:
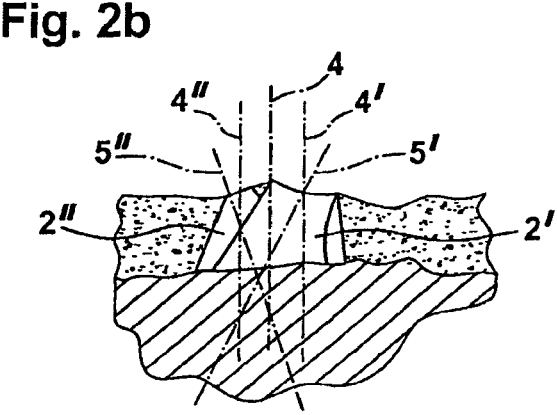

In FIGS. 2a and 2b, a clinical situation with two implants imbedded in a jaw is illustrated in longitudinal section, in which situation a frame 1' instead of a crown is attached to two abutments 2', 2" Implants 3', 3" exhibit axes 5', 5" that may be skew to each other (as shown in FIG. 2b). Abutments 2', 2", however, exhibit insertion axes 4', 4", which are parallel to each other. Implants 3', 3" are anchored in the jawbone 22 and extend to the gum 23.

An ideal abutment also has a cross section formed in such a way that it is twistproof, ie, it prevents the mounted crown from twisting on the abutment.

The outer geometry of the abutment conforms to the minimum dimensions $d_1$, $d_2$, and $d_3$, to be explained below.

Figure 3:
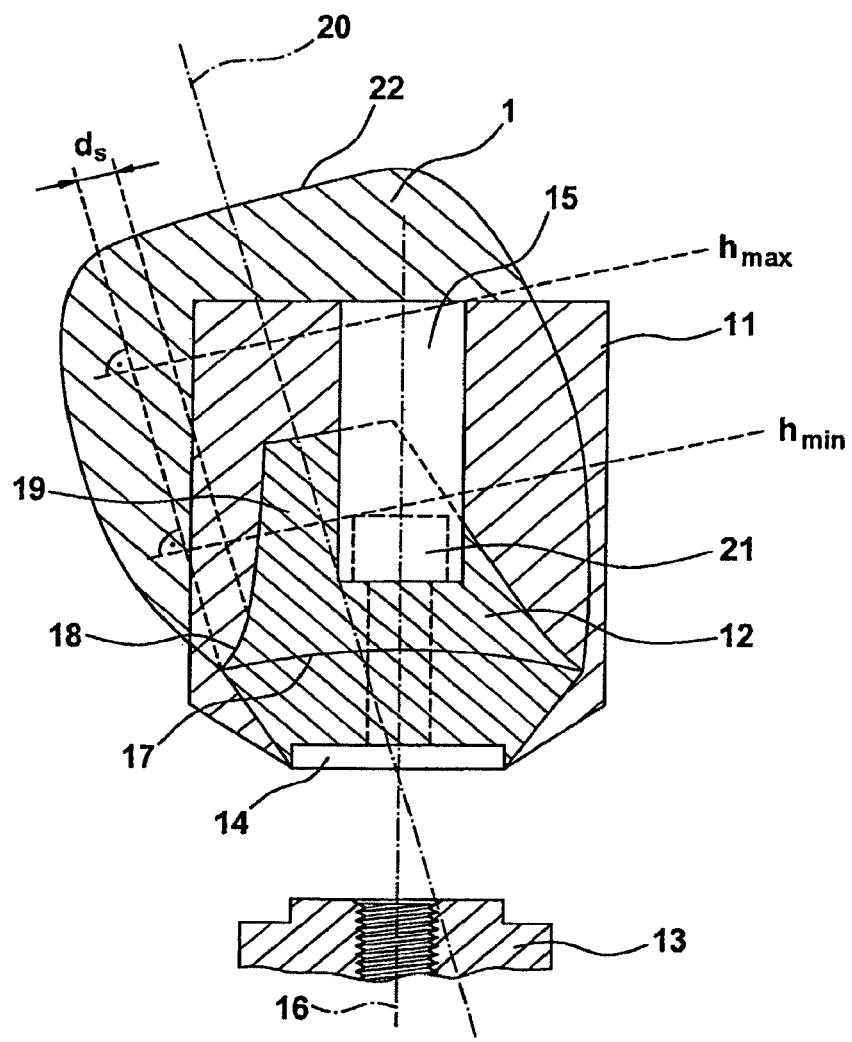
FIG. 3 shows the position of an abutment to be produced in a blank.

FIG. 3 is a diagram of an abutment 12 to be produced from a blank 11. Blank 11 has an attachment geometry 14 for allowing form-fitting attachment to an implant 13, and abutment 12 is positioned in blank 11 in such a way that said abutment will include the attachment geometry 14.

Blank 11 has a bore 15 for the accommodation of a screw for mounting the abutment on the implant. In the present embodiment bore 15 is concentric with a center axis 16 of implant 13. Center axis 16 of implant 13, however, mainly specifies the direction of attachment of attachment geometry 14.

Blank 11 is cone-shaped in the region of the attachment geometry, so that it predefines the design of the abutment toward an abutment edge 17. A shoulder 18 that merges into a post 19 adjoins abutment edge 17.

Post 19 is disposed in blank 11 such that an axis 20 indicating the direction of attachment of crown 1 intersects the center axis 16 at an angle. In principle, axes 16 and 20 can be skew to each other. However, it has been demonstrated that the use of intersecting axes is sufficient.

In this manner there is the assurance that the head 21 (represented by dashed lines) of an occlusal screw lies inside bore 15, which is delimited by the wall of abutment 12.

The optimal abutment shape differs from the ideal abutment shape such that the limiting conditions described below, namely the clinical situation and the technical requirements relating to geometry, material, and fabrication, are fulfilled.

The clinical situation defines the ideal shape of the abutment. The surrounding tooth situation is analyzed in addition to the position and orientation of the dental implant. Such analysis reveals the occlusion direction along with the angle to be compensated by the abutment. The height of the occlusal table is also determined.

The blanks, usually ceramic blocks, that are used to manufacture abutments exhibit certain geometric constraints. Due to precision requirements, the size and shape of these blocks can only be varied to a very limited degree during fabrication. Not just any ideal abutment shape can be produced from these blocks. Among other things, it is important to ensure that head 21 of the occlusal screw disappears completely inside the contours of abutment 12 (see FIG. 3).

The thicknesses of the material and in particular the ceramics used for abutment 2 and crown 1 mounted thereon may not fall below certain minimum values $d_1$, $d_2$, and $d_3$. These wall thicknesses are greatly dependent on the properties of the material used and can therefore be considered separately for each material.

If, when shaping the abutment, any engineering constraints arising from the method of fabricating the abutment and the crown are known, they, too, may influence the optimal shape of the abutment.

If, for example, it is known that both ceramic shapes will be manufactured in a grinding machine having limited degrees of freedom for their tools, it can be confirmed, when generating the optimal shape, whether it is at all possible to shape the abutment by grinding. This applies not only to the positive shape of the abutment but also to its negative shape, that is, the inside of the crown forming an attachment surface.

In order to automatically fabricate the ideal and optimal shape of an abutment, it is first necessary to have a model description of the shape available. In this manner, the abutment edge, for example, can be described as a line in the coordinate system of the implant attachment geometry, and the remaining shape as parameters.

The line defines the transition from the abutment to the crown and is spatially closed. It exists, say, as a list of points or as a function. For esthetic reasons, this line ideally runs somewhat below the surrounding gum tissue.

The shoulder width, the tilt angle, the angle of rotation of the abutment about the longitudinal axis in the blank, and the post height are considered as parameters.

The blank can also be described in terms of the coordinate system of its attachment geometry, which perfectly matches the attachment geometry of the implant. The shape of the ideal abutment edge can then be adjusted little by little locally, so that this line lies completely within the outer contour of the blank 11 used.

To describe the entire abutment, it is merely necessary to optimize all parameters to all constraints. The shoulder width $d_s$ has a minimum value of 1 mm for the standard ceramics used at the present time. The maximum post height $h_{max}$ is delimited by the tilt angle, the block geometry, and the height of occlusal table 22, and lies at least 1 mm below this height. The minimum post height $h_{min}$ is delimited, below, by the position of head 21 of the occlusal screw.

The minimum height $h_{min}$ and the maximum height $h_{max}$ are measured perpendicularly to axis 20, which indicates the direction of attachment of crown 1 on post 19. The minimum shoulder width $d_s$ will be measured parallel to axis 20.

The angle of rotation of the abutment about the longitudinal axis in the blank derives from the relative position of the implant in the clinical situation and, because of the rotational symmetry of the blank, it is not delimited further by said blank.

By using this method, the optimal customized abutment shape is generated automatically and can be fabricated by machining as needed.

At first the clinical situation or a shaped clinical situation of the implant is digitally recorded, for example by means of an intraoral scanning camera. This situation is then analyzed, taking into account the adjacent teeth and the position and orientation of the implant, and the implant axis is defined. This can be accomplished interactively, if desired. After this, all of the data are available for the automatic fabrication of an abutment shape. With the help of the constraints described above, first the ideal abutment shape is computed, and then the optimal abutment shape is computed from said ideal abutment shape.

The separation into two steps is not absolutely necessary, and in particular the user does not have to see the standard abutment computed subsidiarily. For ease of programming, a standard abutment is first computed with reference to the constraining parameters such as the block geometry and the tilt angle, using construction rules, and this abutment is subsequently adjusted to fit the desired profile.

Afterwards the user can focus on the formation of the crown.

Since both elements of the superstructure for the implant are available in digital form, it is possible to ensure an optimum fit between them. The individual elements can be produced at any time with a machining tool from any material, particularly ceramics or metal, but also from plastics material.

Figure 4:
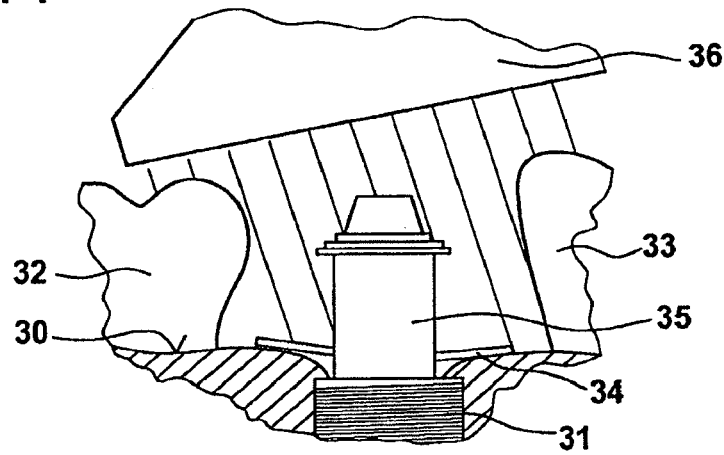
FIG. 4 shows a clinical situation during scanning.

FIG. 4 illustrates an implant 31 inserted in a jawbone (not shown) below the gingival margin 30. On each side of the implant 31 there are adjacent teeth 32, 33, which delimit the boundaries of the lateral span of a superstructure to be constructed. The clinical situation illustrated in FIG. 4 is set up so that the actual course of gingival margin 30 in the immediate vicinity of implant 31 is converted to a desired profile by means of an adjustment piece 34, which profile, together with a measuring device 35 placed on implant 31, is scanned by an intraoral camera 36. The position and orientation of implant 31 can be determined by measuring device 35, and the adjustment piece 34 establishes the gingival profile.

Figure 5:
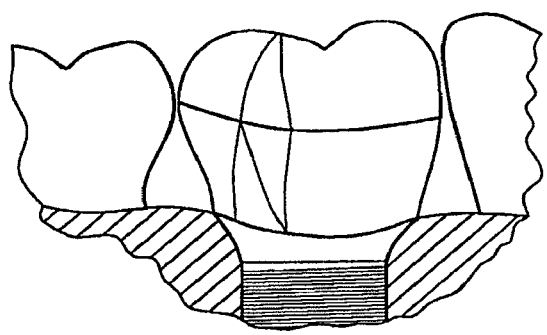
FIG. 5 depicts computation of the superstructure for the clinical situation shown in FIG. 4, FIGS. 6a to 6d show examples of the superstructure dismantled into several elements

A superstructure illustrated in FIG. 5 can be computed on the basis of the scanned data. The size and orientation of the dental crown needed for the implant are defined from the known occlusal surfaces of the adjacent teeth. The cervical finish line of a tooth selected from a dental library is placed in a mesio-distal direction slightly below the level measured by the adjustment piece 34. The cervical surface of the superstructure to be constructed is computed together with the known position of the implant head.

Figure 6A:
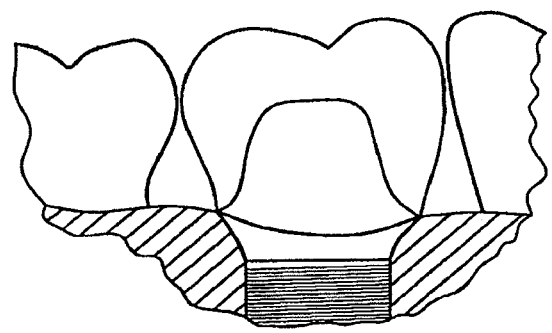

The superstructure in its component two elements is shown diagrammatically in FIG. 6a, said elements consisting of an abutment and a crown, which can be interconnected via a mating surface, also designated as an interface. The design of this interface can be varied within limits by the user, as long as the other construction rules are observed.

The essential factor is that the entire superstructure is computed in this example and that the interface is also automatically determined. This interface allows the user to fabricate the superstructure from more than one piece. This may be necessary for the reason that different restoration materials showing different characteristics may or must be employed, because a design of higher esthetic value is required, or because the geometric conditions permit no other solution.

Figure 6B:
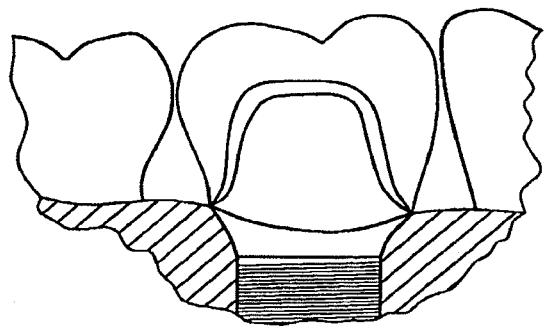

FIG. 6b illustrates a superstructure comprising a cap and an appropriate abutment as components, the cap being veneered with ceramics in conventional manner.

Figure 6C:
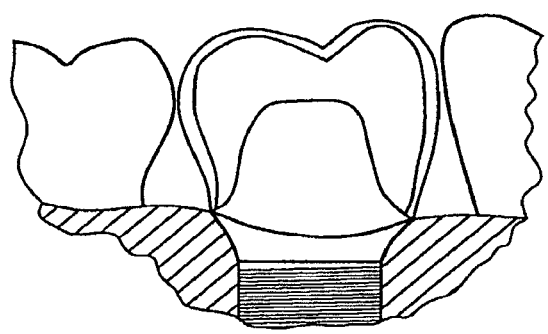

FIG. 6c illustrates a superstructure comprising a reduced crown and an abutment as components of the final replacement. Because of its reduced size, this crown is out of occlusion with the opposing tooth and thus experiences no transferred forces other than residual forces occurring during the process of chewing. In this manner it is possible for the user to design the functionally correct crown as is actually required. This crown is then computationally reduced in size to ensure that it is safely disoccluded. In this case, the element can be produced from, say, plastics material. During a second session, a crown can then be ground according to the original data set and the final crown can be mounted.

Figure 6D:
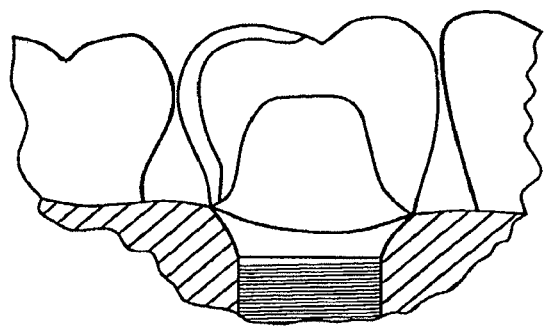

FIG. 6d illustrates a superstructure comprising a partially veneered crown and an abutment as components. The interface between the abutment and the crown as well as that between the crown and the veneer can be computed automatically according to the construction rules.

Figure 7A:
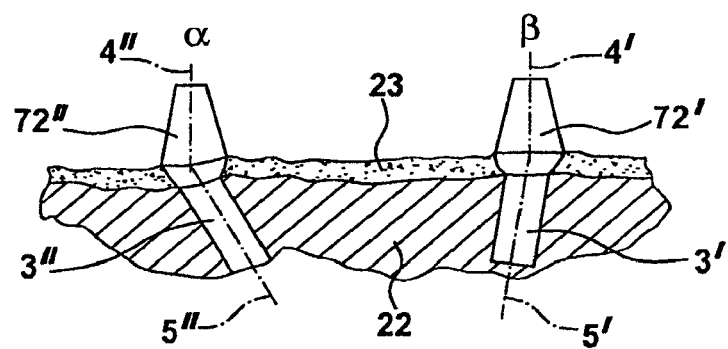
FIGS. 7a and 7b show an exemplary embodiment of conical crowns in two views
Figure 7B:
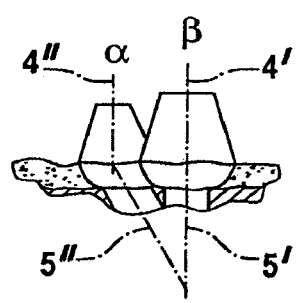

If one or more implants are to be equipped with telescopes or conical crowns, there are in principle two different ways of doing so. The implant, or a plurality of implants, is equipped with a normal abutment, and a telescope crown frame is attached to this abutment, onto which the prosthesis can be pushed. Alternatively, the abutment itself can be designed as a conical crown, as illustrated in FIGS. 7a and 7b. In this case the abutment does not form the usual crown post, but a telescope crown. In this case its shape can be described by a different set of parameters. For example, a line might here again describe the outline shape, whilst additionally the height of the cone and the angle of taper will define the shape within the outline. Implants 3', 3" exhibit axes 5', 5", which may be skewed to each other (as illustrated in FIG. 7a). The conical crowns 72', 72", however, exhibit insertion axes 4', 4" that are parallel to each other. Implants 3', 3" are anchored in jawbone 22 and extend to gingiva 23. The separation into abutment and crown or any other type of subdivision is then computed automatically.

The rules to be observed when shaping the abutment are displayed in the computer and are implemented for automatic splitting to form the abutment and superstructure.

According to EP 1 062 916 A2 either a wax build-up or recourse to a library is used for shaping the abutment as well as the frame and the veneer. If a wax build-up is used, a plurality of scans will have to be made in order to fabricate the abutment, frame, and veneer in succession.

By contrast, the invention accelerates the entire procedure and contributes to making the technology available to the dentist.

Since presently available implants, when they are used to replace individual teeth, cannot be immediately subjected to chewing forces, as that would impair their internal attachment to the jawbone, so-called healing caps are used in the implant systems. After the implant has been inserted, the dentist closes the mechanical connector formed on the implant with a healing cap and sutures the gingiva together. In the course of a second operation approx. 8 weeks later, the dentist reopens the region around the healing cap and then introduces a prosthetic replacement comprising an abutment and a superstructure. In other systems, the healing cap is open and is situated at the level of the gingiva. The healing cap used here also serves to shape the gingiva such that it has a natural profile when compared with the adjacent teeth.

Superstructure 1 can have a plurality of abutments interconnected by a common frame construction (see FIG. 2a).

What is claimed is:

1. A method of automatically fabricating a dental superstructure to be attached to an implant using a digital model description of a shape of the dental superstructure, the dental superstructure including first and second elements, the method comprising:
    recording a real clinical situation or a shaped clinical situation of the implant as digital data;
    analyzing the recorded situation and determining an implant axis and an insertion axis;
    generating digital data representing a shape of the dental superstructure;
    automatically separating the digital data representing the shape of the dental superstructure into first digital data representing a shape of the first element to be connected to the implant and second digital data representing a shape of the second element to be connected to the first element, the shape of the first element being based, at least in part, on a tilt angle between the determined implant axis and the determined insertion axis; and
    fabricating the first and second elements from one or more blanks, based on the first digital data and the second digital data, using machining equipment.

2. The method as defined in claim 1, further comprising determining a mating surface between the first element and the second element.

3. The method as defined in claim 1, wherein the shape of first element of the dental superstructure to be connected to the implant is described by at least two of the following parameters: a shoulder width, the tilt angle, an angle of rotation of the dental superstructure about a longitudinal axis of a blank, and a height of a post.

4. The method as defined in claim 1, wherein one of the first and second elements of the dental superstructure is an abutment and the shape of the abutment is optimized with reference to one or more or all the following parameters:
    a minimum value for a shoulder width;
    a maximum height of a post delimited by the tilt angle, a geometry of a blank, and a height of an occlusal surface, the maximum height of the post being such that the post is disposed at a maximum distance below the height of the occlusal surface;
    a minimum height of the post delimited by the position of a head of an occlusal screw;
    an angle of rotation of the abutment about the longitudinal axis in said blank, the angle of rotation being given by a relative position of said implant in the recorded clinical situation.

5. The method as defined in claim 1, wherein a shape of a blank and the shape of the dental superstructure are described in a coordinate system of a geometry for attachment to said implant.

6. The method as defined in claim 1, further comprising interactively determining the implant axis by a user.

7. The method as defined in claim 1, wherein the first element of the dental superstructure is an abutment and the second element of the dental superstructure is a crown.

8. The method as defined in claim 1, wherein the first element of the dental superstructure is an abutment and the second element of the dental superstructure is a cap.

9. The method as defined in claim 1, wherein the first element of the dental superstructure is an abutment and the second element of the dental superstructure is a reduced crown.

10. The method as defined in claim 1, wherein the dental superstructure includes the first element in a form of an abutment, the second element in a form of a partially veneered crown, and a third element in a form of a veneer, and wherein the method further comprises determining a mating surface between the first and second elements and determining a mating surface between the third element and the first element and/or the second element.

11. The method as defined in claim 1, wherein the dental superstructure includes a number of abutments interconnected by a common frame construction.

12. The method as defined in claim 1, wherein distribution rules can be varied by a user.

13. The method as defined in claim 1, wherein the first element of the dental superstructure to be connected to the implant is computed in a final size of the first element and the second element of the dental superstructure to be connected to the first element is computed as a provisional superstructure having exterior dimensions smaller than final exterior dimensions of the dental superstructure while retaining a mating surface between the first and second elements.

14. The method as defined in claim 13, wherein a same data set is used to compute the first element of the dental superstructure and final dimensions of the provisional superstructure.

15. A method of automatically fabricating a dental superstructure to be attached to an implant using a digital model description of a shape of the dental superstructure, the dental superstructure including first and second elements, the method comprising:

recording a real clinical situation or a shaped clinical situation of the implant as digital data;

analyzing the recorded situation and determining an implant axis and an insertion axis;

generating digital data representing a shape of the dental superstructure;

automatically separating the digital data representing the shape of the dental superstructure into first digital data representing a shape of the first element to be connected to the implant and second digital data representing a shape of the second element to be connected to the first element, the shape of the first element being based, at least in part, on a tilt angle between the determined implant axis and the determined insertion axis; and transmitting the first digital data and the second digital data to machining equipment that fabricates the first and second elements from one or more blanks.

16. The method as defined in claim 15, further comprising determining a mating surface between the first element and the second element.

17. The method as defined in claim 15, wherein the first element of the dental superstructure is an abutment.

* * * * *